United States Patent
Price et al.

(10) Patent No.: US 11,985,999 B2
(45) Date of Patent: *May 21, 2024

(54) METHOD OF IMPROVING FLAVOR OF A COMPOSITION OF (D)-BETA-HYDROXYBUTYRIC ACID AND (D)-1,3 BUTANEDIOL AND USE AS A NUTRITIONAL SUPPLEMENT AND THERAPEUTIC AGENT

(71) Applicant: VitaNav, Inc., Washington, DC (US)

(72) Inventors: Devon Price, Columbia, MD (US); Peter Bayne, Washington, DC (US)

(73) Assignee: VITANAV, INC., Washington, DC (US)

( * ) Notice: Subject to any disclaimer, the term of this patent is extended or adjusted under 35 U.S.C. 154(b) by 185 days.

This patent is subject to a terminal disclaimer.

(21) Appl. No.: 17/498,193

(22) Filed: Oct. 11, 2021

(65) Prior Publication Data

US 2022/0095664 A1     Mar. 31, 2022

Related U.S. Application Data

(62) Division of application No. 17/192,220, filed on Mar. 4, 2021, now Pat. No. 11,141,392.

(60) Provisional application No. 63/079,671, filed on Sep. 17, 2020, provisional application No. 62/985,388, filed on Mar. 5, 2020.

(51) Int. Cl.
| | |
|---|---|
| *A23L 33/10* | (2016.01) |
| *A23F 5/24* | (2006.01) |
| *A23G 3/36* | (2006.01) |
| *A23L 2/54* | (2006.01) |
| *A23L 2/56* | (2006.01) |
| *A23L 2/60* | (2006.01) |
| *A23L 7/126* | (2016.01) |
| *A23L 27/20* | (2016.01) |
| *A23L 33/00* | (2016.01) |
| *A61K 31/047* | (2006.01) |
| *A61K 31/19* | (2006.01) |
| *C12G 3/00* | (2019.01) |

(52) U.S. Cl.
CPC ............ *A23L 33/10* (2016.08); *A23F 5/24* (2013.01); *A23G 3/368* (2013.01); *A23L 2/54* (2013.01); *A23L 2/56* (2013.01); *A23L 2/60* (2013.01); *A23L 7/126* (2016.08); *A23L 27/2026* (2016.08); *A23L 27/2028* (2016.08); *A23L 33/40* (2016.08); *A61K 31/047* (2013.01); *A61K 31/19* (2013.01); *C12G 3/00* (2013.01); *A23V 2002/00* (2013.01)

(58) Field of Classification Search
CPC .......... A23L 33/10; A23L 7/126; A23L 33/40; A23L 5/24; A23L 2/54; A23L 2/56; A23L 2/60; A23L 27/2026; A23L 27/2028; A23G 3/368; C12G 3/00; A61K 31/047; A61K 31/19; A23V 2002/00
See application file for complete search history.

(56) References Cited

U.S. PATENT DOCUMENTS

| | | |
|---|---|---|
| 6,207,856 B1 | 3/2001 | Veech |
| 8,124,589 B2 | 2/2012 | Henderson |
| 8,357,508 B2 | 1/2013 | Mantelatto et al. |
| 9,045,595 B2 | 6/2015 | Mantelatto et al. |
| 10,588,877 B2 | 5/2020 | Arnold |
| 11,044,932 B1 | 6/2021 | Price et al. |
| 2015/0164855 A1 | 6/2015 | Clarke et al. |
| 2017/0013861 A1 | 1/2017 | Nonato et al. |
| 2017/0296501 A1 | 10/2017 | Lowery et al. |
| 2018/0055797 A1 | 3/2018 | Llosa et al. |
| 2018/0057846 A1 | 3/2018 | Llosa et al. |
| 2019/0177673 A1 | 6/2019 | Llosa et al. |
| 2020/0268701 A1 | 8/2020 | D'Agostino et al. |

FOREIGN PATENT DOCUMENTS

BR     1020180740862 A2     6/2020

OTHER PUBLICATIONS

Tzur et al., Adhering to the Ketogenic Diet—Is it Easy or Hard? (Research Review), Nov. 27, 2018, 23 pages. Retrieved from: https://sci-fit.net/adhere-ketogenic-diet.
Cunnane et al., "Can Ketones Help Rescue Brain Fuel Supply in Later Life? Implications for Cognitive Health during Aging and the Treatment of Alzheimer's Disease", Frontiers in Molecular Neuroscience, Jul. 2016, vol. 9, Article 53, 21, pgs.
Dymsza, "Nutritional application and implication of 1,3-butanediol", Fed Proc. Nov. 1975;34(12), pp. 2167-2170.
Fortier et al., "A ketogenic drink improves brain energy and some measures of cognition in mild cognitive Impairment", Alzheimer's & Dementia, 15 (2019), pp. 625-634.
Gajrag et al., "Exogenous ketone supplements: Do they work?", https://www.dietdoctor.com/low-carb/keto/exogenous-ketones#:~:text=We%20will%20find%20out%20just,supplements%20due%20to%20weight%20gain, Nov. 6, 2020, 25 pgs.

(Continued)

*Primary Examiner* — Shirley V Gembeh
(74) *Attorney, Agent, or Firm* — ROTHWELL, FIGG, ERNST & MANBECK, P.C.

(57) ABSTRACT

A method of improving flavor of a combination of a composition for increasing circulating ketone levels is disclosed. A composition containing (D)-β-hydroxybutyric acid (D-BHB), (D)-β-hydroxyvaleric acid (D-BHV), and (D)-1,3 butanediol (D-1,3BD) is disclosed. Exemplary compositions may be incorporated into food, supplement, and beverage products.

20 Claims, 3 Drawing Sheets

(56) References Cited

OTHER PUBLICATIONS

Shivva et al., "An In Silico Knockout Model for Gastrointestinal Absorption Using a Systems Pharmacology Approach—Development and Application for Ketones", PLOS ONE, DOI:10.1371/Journal.pone. 0163795, Sep. 29, 2016, 17 pgs.

Shivva et al., "The Population Pharmacokinetics of D-β-hydroxybutyrate Following Administration of (R)-3- Hydroxybutyl (R)-3-Hydroxybutyrate", The AAPS Journal, vol. 18, No. 3, May 2016, pp. 678-688.

Soto-Mota et al., "Why a d-β-hydroxybutyrate monoester?", Biochem Soc Trans. Feb. 2, 20208; 48(1): 51-59.

Murray et al., "Novel Ketone Diet Enhances Phusical and Cognitive Performance", FASEB J. 30, 4021-4032 (2016).

METHOD OF IMPROVING FLAVOR OF A COMPOSITION OF (D)-BETA-HYDROXYBUTYRIC ACID AND (D)-1,3 BUTANEDIOL AND USE AS A NUTRITIONAL SUPPLEMENT AND THERAPEUTIC AGENT

CROSS REFERENCE TO RELATED APPLICATIONS

This application is a Divisional of U.S. Ser. No. 17/192,220 filed Mar. 4, 2021, which claims the benefit of U.S. Provisional Application No. 62/985,388 filed on Mar. 5, 2020, and U.S. Provisional Application No. 63/079,671 filed on Sep. 17, 2020, the disclosures of which are hereby incorporated by reference in their entireties.

FIELD

This disclosure relates to a new and nonobvious method of improving the flavor of a composition including (D)-β-hydroxybutyric acid, and (D)-1,3 butanediol. The disclosure also relates to a methods for improving the performance of ketone bodies in a food or beverage product by combining at least (D)-β-hydroxybutyric acid and (D)-1,3 butanediol.

BACKGROUND

During periods of carbohydrate deprivation, the body utilizes energy obtained from the metabolism of fats. During fat metabolism, fats are converted to ketone bodies. Large quantities of these substances accumulate in the blood. This condition, which is known as ketosis, is known to occur during starvation. When blood ketone body concentrations are elevated to levels found in prolonged starvation, they provide a significant source of energy for the brain and body. Studies of certain states of ketosis have led to the recognition that those states can deliver health benefits. For example, certain states of ketosis are understood to play a positive role in aging pathways and in treatment of symptoms of epilepsy, neurodegenerative diseases, heart disease and type II diabetes. Known methods of accessing the energy and health benefits ketones provide are often not effective, and all solutions, regardless of efficacy, are not well tolerated and therefore not readily available to most of the general population.

The most common method of elevating circulating ketone levels is through diet-depriving the body of glucose by fasting or adhering to a ketogenic diet such that metabolism switches from using glucose to ketones produced endogenously from fatty acids. These diets can be difficult to adhere to on a long-term basis and are impractical for most people.

Exogenous sources of ketones including ingestible ketone bodies and their precursors may prevent the need for extended fasting or ketogenic diets to elevate circulating ketone levels. However, each of the known ingestible ketone bodies also has drawbacks limiting their use.

D 1,3 butanediol for example, is a metabolic precursor to D-β-hydroxybutyrate (D-BHB) and may be used as source of calories. However, D 1,3 butanediol has an unpleasant bitter flavor preventing it from playing a significant role in the food supply.

Another example of an ingestible ketone body precursor is racemic 1, 3-butanediol. Racemic 1, 3-butanediol can cause unwanted side effects. For example, non-physiological isomers, such as (L)-β-hydroxybutyrate can act as competitive inhibitors to ketone body transport. Ketone body transport across the blood-brain barrier is a limiting factor to ketone body metabolism in the brain.

The ketone body D-beta hydroxybutyric acid is another source of exogenous ketones. One of the well-known problems with beta hydroxybutyric acid, however, is that it is very acidic. D-beta hydroxybutyric acid has a pH similar to lemon juice of 2.5. Because of this acidity the quantity and concentration in which D-beta hydroxybutyric acid may be used in ingestible form is limited. Direct administration of large quantities of D-β-hydroxybutyrate or acetoacetate in their acid form can result in acidosis following rapid absorption from the gastrointestinal tract.

Ketone body concentrations may also be elevated by administering a cyclic trimer of D-β-hydroxybutyrate (triolide) as a metabolic precursor for D-β-hydroxybutyrate. However, the triolide is not efficiently hydrolyzed by gastric enzymes and thus is poorly absorbed. This limits its usefulness as a (R)-3-hydroxybutyrate precursor.

The acidity problem with D-BHB acid has been addressed in some applications by combining D-BHB with sodium, magnesium, calcium and potassium salts (D'Agostino, U.S. 2020/0268701A1). This approach doesn't fully address the problem, however. While the salts address the acidity problem, use of ketone salts is limited to very small nutritionally and therapeutically irrelevant amounts due to the high accompanying salt load. In addition to the small dosage, the taste is also unpleasant.

Ketone ester compounds—another metabolic precursor—as disclosed in U.S. Pat. No. 8,642,654, avoid the salt load problem and can be administered in high concentrations to induce ketosis. Ketone esters generally have a toxic flavor thus limiting their use as a supplement or therapeutic agent.

Thus, ingesting sufficient amounts of D-BHB in an acid or salt form to achieve ketosis is not viable due to the accompanying acid/salt load as well as gastrointestinal side effects. Ingestion of such compounds is also associated with sleep loss. Often, ingestion of commercial compositions containing such ketone salt or ketone ester compounds fails to result in a sufficient plasma level increase. For example, ingestion of commercial compositions containing such ketone salt or ketone ester compounds often results in a 0.5 mM or lower increase in circulating ketone levels, which does not provide a cognitive or physical benefit. Often, ingestion of commercial compositions containing such ketone salt or ketone ester compounds is intolerable multiple times daily or for an extended number of days or weeks. As such, existing products are associated with poor taste, poor bioavailability, poor tolerability, and side effects. Further, such existing ketone salt products provide relatively low amounts of ketone compounds at high cost, making their benefits, if any, too low relative to their cost.

There is a long-felt and unmet need to augment the food supply and make the health benefits of ketones readily available to the mainstream market in a composition that efficiently induces ketosis without restriction, is well-tolerated, and tastes good. Additionally, it would be beneficial to have a composition that can be more cost-effective and more efficient than prior methods of inducing ketosis.

SUMMARY OF THE INVENTION

Disclosed herein are novel combinations of (D)-β-hydroxybutyric acid, (D)-β-hydroxyvaleric acid, and (D)-1,3 butanediol and compositions that include these components. Food and beverage products including a novel combination of these compositions are also disclosed. These novel compositions can taste better, avoid acidity issues, and thus can result in superior palatability when compared with other exogenous ketone compositions. Moreover, the combinations disclosed herein can have a greater efficacy than other exogenous ketone compositions. When administered to a subject, these combinations of (D)-β-hydroxybutyric acid, (D)-β-hydroxyvaleric acid, and (D)-1,3 butanediol exhibit properties that are greater than administration of either constituent individually. Thus, disclosed examples permit achieving nutritional and therapeutic benefits of circulating ketone bodies using less material than would otherwise be required. Furthermore, drawbacks limiting use of ketone body precursors may be avoided. These benefits can be obtained while providing a better tasting compound that is likely to be better tolerated by the person consuming the composition.

Examples disclosed herein can induce functional ketosis to a greater extent than known compositions. Ketone bodies have been found to have a range of potential benefits, from treatment of diabetes and neurodegenerative disease symptoms, to enhanced cognitive health and endurance performance in athletes. Examples disclosed herein have the potential to yield higher net elevation of circulating ketones over time in an individual. When administered in therapeutically effective amounts, the disclosed combination of compositions can produce a higher degree of ketotic efficiency than other known ketone body supplements.

Also disclosed is a method of improving the flavor profile of a food or beverage product including ketone bodies. The method can include adding (D)-1,3 butanediol to (D)-β-hydroxybutyric acid in a specific ratio as disclosed herein. Optionally, (D)-β-hydroxyvaleric acid may also be included in the composition. The method may include using the (D)-1,3 butanediol as a solvent for flavorings. For example, a source of flavoring such as fruit may be added to (D)-1,3 butanediol. The fruit may be added to the (D)-1,3 butanediol for a predetermined amount of time to allow the flavorings to enter a solution. In one example, the fruit may be freeze dried fruit. After a desired amount of flavoring has entered the solution, the solution can be filtered to remove fiber, pulp, and other undesirable components. This resulting solution can then be added to (D)-β-hydroxybutyric acid. In another example, the resulting flavored solution including (D)-1,3 butanediol may be added to (D)-β-hydroxybutyric acid and (D)-β-hydroxyvaleric acid. According to certain embodiments, a beverage may be created by including a substantial amount of consumable liquid, such as water. A beverage may include carbonation. A food product may be produced by including an amount of a consumable (edible) solid, liquid, or gel. In some aspects, the product may include a slowly dissolving or slowly digesting matrix. In some aspects a slowly digesting matrix may include fibers and carbohydrates having a glycemic index of less than 70, e.g., 40 to 65, 62, 60, 57, 55 or lower.

Other features and characteristics of the subject matter of this disclosure, as well as the methods of operation, functions of related elements of structure and the combination of parts, and economies of manufacture, will become more apparent upon consideration of the following description and the appended claims, all of which form a part of this specification.

BRIEF DESCRIPTION OF THE DRAWINGS

Various features of examples and embodiments in accordance with the principles described herein may be more readily understood with reference to the following detailed description taken in conjunction with the accompanying drawings, where like reference numerals designate like structural elements, and in which.

DETAILED DESCRIPTION

Figure 1:
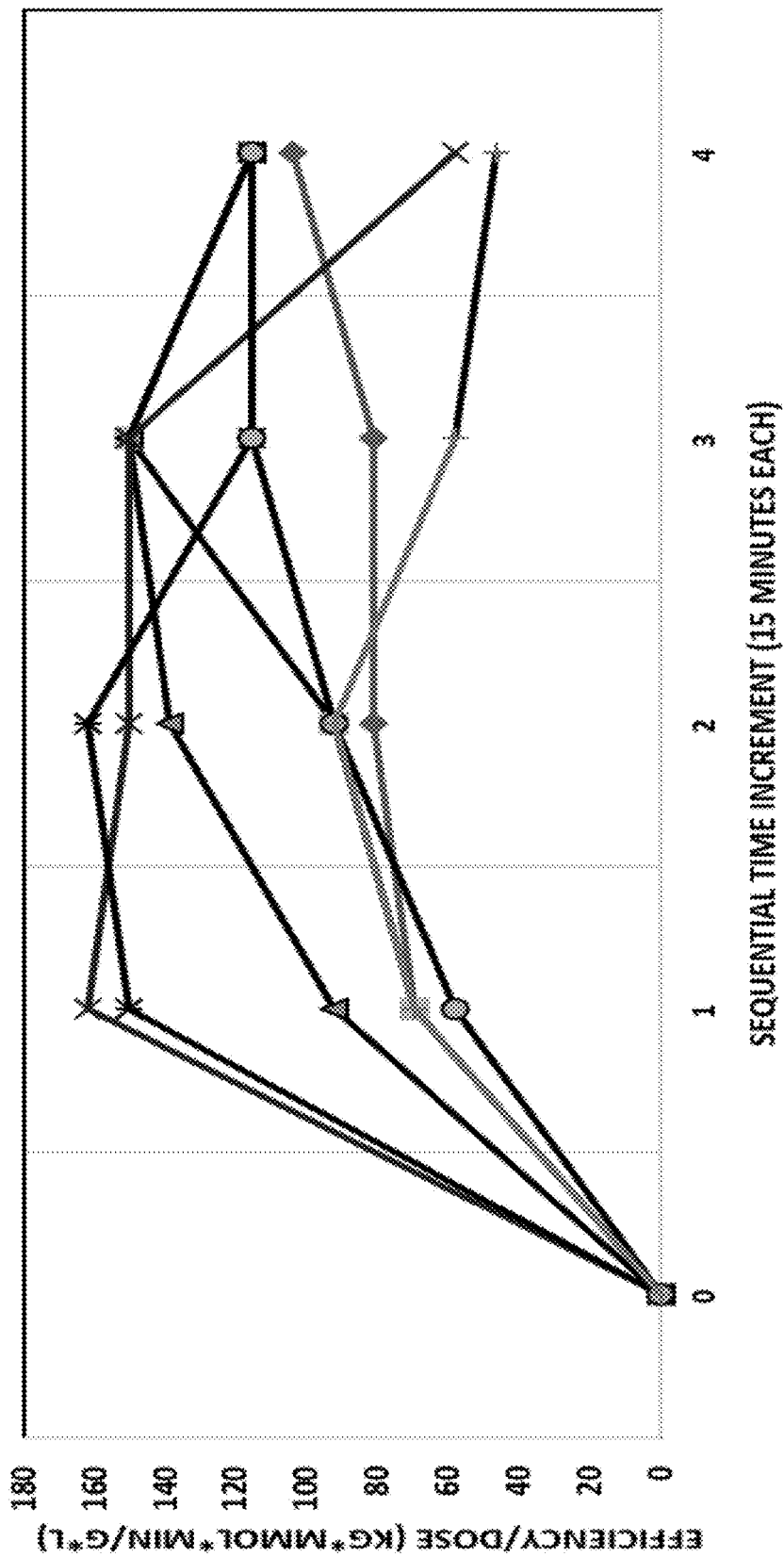
FIG. 1 represents the results of administration of (D)-β-hydroxybutyric acid, (D)-β-hydroxyvaleric acid and (D)-1,3 butanediol over the course of a 60-minute period in various ratios in a subject at rest.

While aspects of the subject matter of the present disclosure may be embodied in a variety of forms, the following description is merely intended to disclose some of these forms as specific examples of the subject matter encompassed by the present disclosure. Accordingly, the subject matter of this disclosure is not intended to be limited to the forms or embodiments so described.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 0.01 to 2.0" should be interpreted to include not only the explicitly recited values of about 0.01 to about 2.0, but also include individual values and sub-ranges within the indicated range. Thus, included in this numerical range are individual values such as 0.5, 0.7, and 1.5, and sub-ranges such as from 0.5 to 1.7, 0.7 to 1.5, and from 1.0 to 1.5, etc. Furthermore, such an interpretation should apply regardless of the breadth of the range or the characteristics being described. Additionally, it is noted that all percentages are in weight, unless specified otherwise.

In understanding the scope of the present disclosure, the terms "including" or "comprising" and their derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps. It is understood that reference to any one of these transition terms (i.e. "comprising," "consisting," or "consisting essentially") provides direct support for replacement to any of the other transition term not specifically used. For example, amending a term from "comprising" to "consisting essentially of" would find direct support due to this definition.

As used herein, the terms "about" and "approximately" are used to provide flexibility to a numerical range endpoint by providing that a given value may be "a little above" or "a little below" the endpoint. The degree of flexibility of this term can be dictated by the particular variable and would be within the knowledge of those skilled in the art to determine based on experience and the associated description herein. For example, in one aspect, the degree of flexibility can be within about ±10% of the numerical value. In another aspect, the degree of flexibility can be within about ±5% of the numerical value. In a further aspect, the degree of flexibility can be within about ±2%, ±1%, or ±0.05%, of the numerical value.

As used herein, a plurality of compounds, elements, or steps may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Furthermore, certain compositions, elements, excipients, ingredients, disorders, conditions, properties, steps, or the like may be discussed in the context of one specific embodiment or aspect or in a separate paragraph or section of this disclosure. It is understood that this is merely for convenience and brevity, and any such disclosure is equally applicable to and intended to be combined with any other embodiments or aspects found anywhere in the present disclosure and claims, which all form the application and claimed invention at the filing date.

As used herein, the phrase "substantially no" may refer to a composition containing less than 1, 0.9, 0.8, 0.7, 0.6, 0.5, 0.4, 0.3, 0.2, 0.1, 0.09, 0.08, 0.07, 0.06, 0.05, 0.04, 0.03, 0.02, or 0.01 wt % of a specified ingredient. In some aspects, the phrase "substantially no" may refer to a composition containing trace amounts of a specified ingredient. In some aspects, the phrase "substantially no" may refer to a composition containing a specified ingredient below a level of detection.

In some aspects, the present disclosure includes using an enantiomerically pure form of a compound, e.g., greater than 95, 96, 97, 98, 99, or 99.5% enantiomerically pure.

Throughout this description, the preferred embodiments and examples provided herein should be considered as exemplary, rather than as limitations, of the present invention.

In a first aspect, the present disclosure provides a combination of (D)-β-hydroxybutyric acid ("D-BHB") and (D)-1,3 butanediol ("D-1,3BD". In a further aspect, the present disclosure provides a combination of D-BHB, (D)-β-hydroxyvaleric acid ("D-BHV"), and D-1,3BD. Numerous non-limiting examples providing exemplary proportions of these compounds are provided. These combinations and compositions containing such combinations may be prepared as food and beverage products for human consumption, thereby providing a dietary source of exogenous ketones. The resulting mixture can exhibit reduced acidity, better flavoring, and reduce or avoid the need to add additional salts to the composition to improve palatability. Moreover, the combinations disclosed herein can have a greater efficacy than other exogenous ketone compositions. When administered to a subject, the disclosed combinations of D-BHB and D-1,3BD and the disclosed combinations of D-BHB, D-BHV, and D-1,3BD exhibit an increase in blood ketones that is greater than administration of either constituent individually. Thus, the disclosed examples permit achieving nutritional and therapeutic benefits of sufficiently high circulating ketone bodies using less material than would otherwise be required.

As used herein, the terms "administer" and "administration" will include self-administration, ingestion, or consumption by a subject. In other words, the terms will include methods that result in consumption of the disclosed products by a subject. As such, methods of the present disclosure will include making, using, selling, offering for sale, importing, or exporting any of the products or compositions of the present disclosure intended for consumption or use in producing a consumable product.

In one aspect, the present disclosure provides a composition having 25% to 85% by weight of (D)-β-hydroxybutyric acid and 15% to 75% by weight of (D)-1,3 butanediol. In one aspect, the present disclosure provides a composition having 25% to 85% by weight of a mixture of (D)-β-hydroxybutyric acid and (D)-β-hydroxyvaleric acid and 15% to 75% by weight of (D)-1,3 butanediol. In one aspect, the molar ratio of (D)-β-hydroxybutyric acid to (D)-β-hydroxyvaleric acid may be between 1.0 to 0.01 and 0.7 to 0.3. In one aspect, the present disclosure provides a composition having (D)-β-hydroxybutyric acid and (D)-1,3 butanediol in a molar ratio range of 3:7 to 7:3. In one aspect, the present disclosure provides a composition having (D)-β-hydroxybutyric acid and (D)-1,3 butanediol in a molar ratio range of 4:6 to 6:4. In one aspect, the present disclosure provides a composition having (D)-β-hydroxybutyric acid and (D)-1,3 butanediol in a 1:1 molar ratio. In one aspect, the present disclosure provides a composition having 25% to 75% by molar of a mixture of (D)-β-hydroxybutyric acid and (D)-β-hydroxyvaleric acid and 25% to 75% by weight of (D)-1,3 butanediol. In one aspect, the present disclosure provides a composition having 35% to 70% by weight of a mixture of (D)-β-hydroxybutyric acid and (D)-β-hydroxyvaleric acid and 30% to 65% by weight of (D)-1,3 butanediol. In one aspect, the present disclosure provides a composition having 45% to 55% by weight of a mixture of (D)-β-hydroxybutyric acid and (D)-β-hydroxyvaleric acid and 55% to 45% by weight of (D)-1,3 butanediol. In one aspect, the present disclosure provides a composition having 48% to 52% by weight of a mixture of (D)-β-hydroxybutyric acid and (D)-β-hydroxyvaleric acid and 48% to 52% by weight of (D)-1,3 butanediol.

In one aspect, a composition, beverage or food product of the present disclosure may contain at least 5, 10, 20, 30, 40, 50, 60, 70, 80, or 90% of the D)-β-hydroxybutyric acid, the (D)-β-hydroxyvaleric acid, or both, in the form of a magnesium salt, potassium salt, sodium salt, calcium salt, or combination thereof. In some aspects, the composition, beverage or food product of the present disclosure may contain up to 50% of the D)-β-hydroxybutyric acid, the (D)-β-hydroxyvaleric acid, or both, in the form of a magnesium or potassium salt. In some aspects, the composition, beverage or food product of the present disclosure may contain up to 30% of the D)-β-hydroxybutyric acid, the (D)-β-hydroxyvaleric acid, or both, in the form of a calcium salt. In some aspects, the composition, beverage or food product of the present disclosure may contain up to 60% of the D)-β-hydroxybutyric acid, the (D)-β-hydroxyvaleric acid, or both, in the form of a combination of magnesium, potassium, and/or calcium salts.

In another aspect, the present disclosure provides a method and composition for increasing plasma levels of ketone bodies in a human subject by 30, 40, 50%, 60% or more compared to administration of an equivalent amount by weight of (D)-β-hydroxybutyrate or (D)-1,3 butanediol alone by administering the compositions of the present disclosure.

In another aspect, the present disclosure provides a method and composition for inducing a D-BHB plasma level increase of at least 1.4 mM within 2 hours by administering the compositions of the present disclosure.

In another aspect, the present disclosure provides a method and composition for inducing a D-BHB plasma level increase of at least 1.5 mM within 2 hours by administering the compositions of the present disclosure.

In another aspect, the present disclosure provides a method and composition for inducing a D-BHB plasma level increase of at least 2.0 mM within 2 hours by administering the compositions of the present disclosure.

In another aspect, the present disclosure provides a method and composition for maintaining a D-BHB plasma level increase of at least 1.4 mM for 2.5 hours by administering the compositions of the present disclosure.

In another aspect, the present disclosure provides a method and composition for maintaining a D-BHB plasma level increase of at least 1.4 mM for 3 hours by administering the compositions of the present disclosure.

In another aspect, the present disclosure provides a method and composition for maintaining a D-BHB plasma level increase of at least 1.4 mM for 3.5 hours by administering the compositions of the present disclosure.

In another aspect, the present disclosure provides a method and composition for maintaining a D-BHB plasma level increase of at least 1.4, 1.5, 1.6, 1.7, 1.8, 1.9, or 2 mM for 2, 2.5, 3, 3.5, or 4 hours by administering the compositions of the present disclosure.

In another aspect, the present disclosure provides a method and composition that is tolerable and sufficiently palatable for daily use by a human subject for at least 12, 26, 52 weeks, or longer by administering the compositions of the present disclosure.

In another aspect, the present disclosure provides a method and composition that is tolerable and sufficiently palatable for use 1, 2, 3, 4, 5, or 6 times daily by a human subject for at least 12, 26, 52 weeks, or longer by administering the compositions of the present disclosure.

In another aspect, the present disclosure provides a method of reducing or avoiding gastrointestinal side effects associated with ingestion of salts or esters of D-BHB and D-1,3BD or compositions containing D-BHB or D-1,3BD as single agents by administering the compositions of the present disclosure.

In another aspect, the present disclosure provides a method of reducing or avoiding sleep loss associated with ingestion of salts or esters of D-BHB and D-1,3BD or compositions containing D-BHB or D-1,3BD as single agents by administering the compositions of the present disclosure.

In another aspect, the present disclosure provides a method of increasing slow wave sleep (SWS) duration by at least 10, 20, 30, 40, or 50% relative to compositions and methods of ingestion of salts or esters of D-BHB and D-1,3BD or compositions containing D-BHB or D-1,3BD as single agents, by administering the compositions of the present disclosure.

In another aspect, the present disclosure provides a method of increasing rapid eye movement (REM) sleep duration by at least 10, 20, 30, 40, or 50% relative to compositions and methods of ingestion of salts or esters of D-BHB and D-1,3BD or compositions containing D-BHB or D-1,3BD as single agents, by administering the compositions of the present disclosure.

Example 1

According to a first example, a composition includes approximately 85% D-BHB and approximately 15% D-1,3BD. In this example, there may be substantially no D-BHV present in the composition.

Example 2

According to a second example, a composition includes approximately 59% D-BHB, approximately 26% D-BHV, and approximately 15% D-1,3BD. This example is similar to Example 1 except that D-BHV is present instead of some of the D-BHB in the resulting composition.

Example 3

According to a third example, a composition includes approximately 25% D-BHB and approximately 75% D-1,3BD. In this example, there may be substantially no D-BHV present in the composition.

Example 4

According to a fourth example, a composition includes approximately 17% D-BHB, approximately 8% D-BHV, and 75% D-1,3BD. This example is similar to Example 3 except that D-BHV is present instead of some of the D-BHB in the resulting composition.

Example 5

According to a fifth example, a composition includes approximately 46% D-BHB, approximately 4% D-BHV, and approximately 50% D-1,3BD.

Example 6

According to a sixth example, a composition includes approximately 40% D-BHB, approximately 10% D-BHV, and approximately 50% D-1,3BD.

Example 7

According to a seventh example, a composition includes approximately 23% D-BHB, approximately 2% D-BHV, and approximately 75% D-1,3BD.

Example 8

According to an eighth example, a composition includes approximately 20% D-BHB, approximately 5% D-BHV, and approximately 75% D-1,3BD.

Example 9

According to a ninth example, a composition includes approximately 64% D-BHB, approximately 1% D-BHV, and approximately 35% D-1,3BD.

Example 10

According to a tenth example, a composition includes approximately 59% D-BHB, approximately 6% D-BHV, and approximately 35% D-1,3BD.

Example 11

According to a eleventh example, a composition includes approximately 44% D-BHB, approximately 1% D-BHV, and approximately 55% D-1,3BD.

Example 12

According to a twelfth example, a composition includes approximately 41% D-BHB, approximately 4% D-BHV, and approximately 55% D-1,3BD.

Example 13

According to a thirteenth example, a composition includes approximately 84% D-BHB, approximately 1% D-BHV, and approximately 15% D-1,3BD.

Example 14

According to a fourteenth example, a composition includes approximately 72% D-BHB, approximately 13% D-BHV, and approximately 15% D-1,3BD.

Example 15

According to a fifteenth example, a composition includes approximately 59% D-BHB, approximately 1% D-BHV, and approximately 40% D-1,3BD.

Example 16

According to a sixteenth example, a composition includes approximately 51% D-BHB, approximately 9% D-BHV, and approximately 40% D-1,3BD.

In accordance with examples 1 to 4, the weight percentage of D-BHB and D-BHV can range between approximately 25% and approximately 85%. The percentage by weight of D-BHB to D-BHV may be varied within this range. The amount of D-BHV by weight of the composition may range, for example, between substantially 0% to approximately 26% D-BHV. Additionally, in these examples, the percentage by weight of D-1,3BD can range from approximately 15% to approximately 75% by weight.

In accordance with examples 5 to 8, the weight percentage of D-BHB and D-BHV can range between approximately 25% and approximately 50%. The percentage by weight of D-BHB to D-BHV may be varied within this range. The amount of D-BHV by weight of the composition may range, for example, between approximately 2% to approximately 10%. Additionally, in these examples, the percentage by weight of D-1,3BD can range from approximately 50% to about 75% by weight.

In accordance with examples 9 to 12, the weight percentage of D-BHB and D-BHV can range between approximately 45% and approximately 65%. The percentage by weight of D-BHB to D-BHV may be varied within this range. The amount of D-BHV by weight of the composition may range, for example, between approximately 1% to approximately 6%. Additionally, in these examples, the percentage by weight of D-1,3BD can range from approximately 35% to about 55% by weight.

In accordance with examples 13 to 16, the weight percentage of D-BHB and D-BHV can range between approximately 60% and approximately 85%. The percentage by weight of D-BHB to D-BHV may be varied within this range. The amount of D-BHV by weight of the composition may range, for example, between approximately 1% to approximately 9%. Additionally, in these examples, the percentage by weight of D-1,3BD can range from approximately 15% to about 40% by weight.

In accordance with each of the examples above, a general exemplary composition disclosed herein includes between approximately 15% to approximately 85% D-BHB, between substantially no D-BHV to approximately 26% D-BHV, and between approximately 15% to approximately 75% D-1,3BD. Various examples of this general composition are given, but are not intended to be presented to the exclusion of compositions within the various disclosed ranges.

The administration of examples presented herein result in an increase in the circulating level of ketones in a human subject at rest that is greater than would result from the administration of (D)-β-hydroxybutyrate or (D)-1,3 butanediol alone over a duration of, for example, 120 minutes. Some examples include administration of a combination of D-BHB, D-BHV, and D-1,3BD in a therapeutically effective amount such that the rate change of circulating ketones in the blood of a human subject at rest is faster than the administration of an equivalent amount of either D-BHB or D-1,3BD administered alone. In one example, this includes the administration of a composition including a mixture of 45% D-BHB and 55% D-1,3BD. In one example, this includes the administration of a composition including a mixture of 43.2%% D-BHB, 1.8% D-BHV and 55% D-1,3BD. In another example, this includes the administration of a composition including a mixture of 52.8% DBHB, 2.2% D-BHV, and 45% D-1,3BD. In another example, this includes the administration of at composition including a mixture of 62.4% D-BHB, 2.6% D-BHV, and 35% D-1,3BD.

FIG. 1 shows the results of administration of D-BHB, D-BHV, and D-1,3BD over the course of a 60-minute period in various ratios in a subject at rest. Examples include using a composition including D-BHB, D-BHV, and D-1,3BD in a subject at rest. The ketotic efficiency represents the net elevation of circulating ketones a ketone supplement affects over time in an individual. Ketotic efficiency may be represented as:

$$\Sigma_{t=0}{}^{n}(\text{mMol/L})/(\text{g/kg})*t$$

where mMol/L is the concentration of circulating β-hydroxybutyrate in the blood, g is the total dose of the combined D-BHB, D-BHV, and D-1,3,BD in grams, kg is the mass of the individual in kilograms, and t is an increment of time in minutes.

The ketotic efficiency of the D-BHB, D-BHV, and D-1,3BD blend measured over of one hour in this exemplary study is 43% to 104% greater than the administration of pure (D)-1,3 butanediol or pure (D)-β-hydroxybutyric acid alone, respectively. While this example pertains to a fasted subject at rest, the relative utility of blended vs pure constituents has also been observed in fed and active subjects.

As illustrated by the examples of FIG. 1, these exemplary compositions can advantageously elevate circulating ketones by approximately two times greater than other known compositions. Such a composition can sustain ketonemia for longer than either D-BHB or D-1,3BD can when ingested alone by a subject of a given weight as shown by the 100% line (i.e., contains D-BHB, but not D-1,3BD) and the 0% line (i.e., contains only D-1,3BD, but not D-BHB).

As shown in the following table, the increase in circulating ketone level with a 10 g dose in three human subjects at rest was maximal at between 45-55% D-BHB in the tested compositions.

| % D-BHB Acid | Max change in mMol/L |
| --- | --- |
| 100% | 0.9 |
| 85% | 1.3 |
| 65% | 1.3 |
| 55% | 1.4 |
| 45% | 1.4 |
| 25% | 1 |
| 0% | 0.8 |

Figure 2:
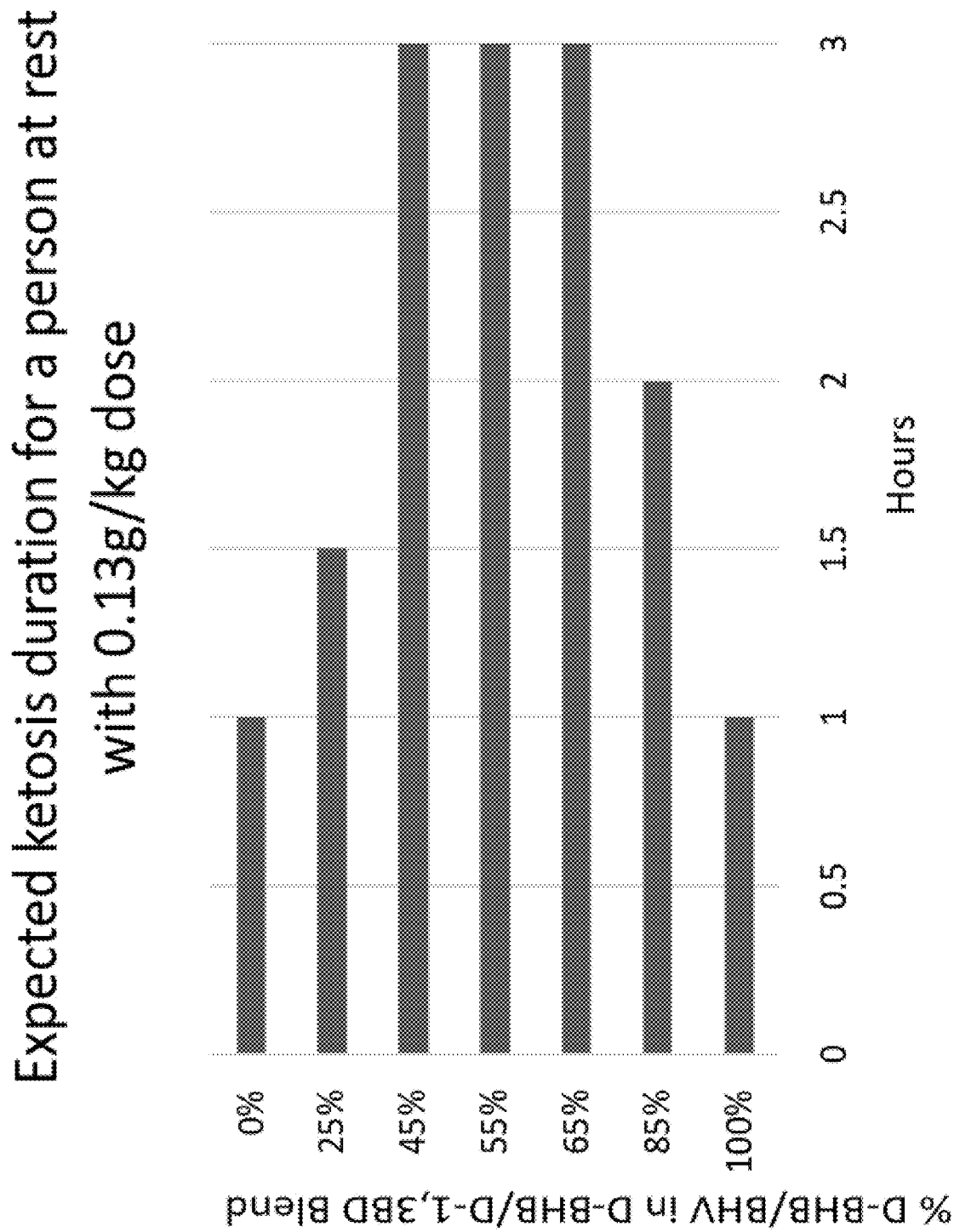
FIG. 2 represents the expected ketosis for a subject at rest with a 0.13 g/kg dose of (D)-β-hydroxybutyric acid, (D)-β-hydroxyvaleric acid and (D)-1,3 butanediol over time for the periods shown.

FIG. 2 represents the expected ketosis for a person at rest with a 0.13 g/kg dose of (D)-β-hydroxybutyric acid, (D)-β-hydroxyvaleric acid, and (D)-1,3 butanediol over time for the periods shown. For instance, based on the measured plasma levels illustrated in FIG. 1, it can be concluded that administration of 100% D-1,3BD does not cause a prolonged rise of blood ketone levels. A similar result was obtained upon administration of 100% D-BHB. Administration of examples in accordance with the present disclosure are expected to cause efficient, prolonged rises in circulating blood ketone levels in a manner that is unexpected based on the current literature. As shown in the following table, the highest efficiency at both 1 and 2 hours post-administration was obtained at 45% D-BHB+D-BHV (0.96:0.04) to 55% D-1,3BD and the lowest efficiency was observed when administering D-BHB or D-1,3BD alone.

| Concentration of DBHB + DBHV in a compositing containing DBHB + DBHV and D-1,3BD | 1 hour ketotic efficiency (kg*Mmol*min/g*L) | 2 hours ketotic efficiency (kg*Mmol*min/g*L) |
| --- | --- | --- |
| 100% | 335 | 566 |
| 85% | 427 | 739 |
| 65% | 497 | 780 |
| 55% | 520 | 774 |
| 45% | 543 | 826 |
| 25% | 381 | 739 |
| 0% | 266 | 462 |

As demonstrated herein, the combination of the present disclosure safely induces ketosis more rapidly than previously thought possible. For example, U.S. Pat. No. 9,138,420 shows that a peak concentration of blood concentrations of (D)-β-hydroxybutyrate produced by consuming a combination of (D/L)-β-hydroxybutyrate salt and MCT (medium chain triglycerides) oil required up to 3 hours.

The present disclosure includes mixing D-BHB, D-BHV, and D-1,3BD in a food or beverage product. For example, any of the compositions according to the examples, discussed earlier, may be included within a beverage or food product. Still further examples include the administration of the disclosed compositions of D-BHB, D-BHV, and D-1,3BD as a nutritional supplement to induce ketonemia. Still further examples include the administration of the disclosed compositions including D-BHB, D-BHV, and D-1,3BD as a nutritional supplement to increase cognitive and physical endurance and performance, reduce food cravings, and increase appetite control.

An example of a method includes administering a composition to a human subject in a beverage or food product. In one aspect, the beverage or food product may be designed to be consumed in one sitting rather than over a prolonged period. The exemplary compositions described in the non-limiting examples and other disclosures provided herein may be used in such beverage or food products.

In some aspects, the present disclosure involves a unit dosage containing about 5 grams or more of the combination of D-BHB, D-BHV, and D-1,3BD of the present disclosure. In some aspects, the present disclosure involves a unit dosage containing 5-50, 6 to 49, 7 to 48, 8 to 47, 8 to 46, 9 to 45, 10 to 44, 11 to 43, 12 to 42, 13 to 40, 14 to 35, 15 to 30, 16-25, or 18 to 22 grams of the combination of D-BHB, D-BHV, and D-1,3BD of the present disclosure. In some aspects, the present disclosure includes a composition or method for inducing and maintaining ketonemia or ketosis by ingesting at least 10 grams of the combination of D-BHB, D-BHV, and D-1,3BD of the present disclosure daily (e.g., 1, 2, 3, 4, 5, 6, or more times per day). In some aspects, the present disclosure includes a composition or method for inducing and maintaining ketonemia or ketosis by ingesting at least 10 grams of the combination of D-BHB, D-BHV, and D-1,3BD of the present disclosure weekly (e.g., 5, 6, 7, 8, 9, 10, 12, 14, 21, 28 or more times per week). In some aspects, the present disclosure includes a composition or method for inducing and maintaining ketonemia or ketosis by ingesting at least 10 grams of the combination of D-BHB, D-BHV, and D-1,3BD of the present disclosure every 2, 3, 4, or 5 hours. In some aspects, the present disclosure includes a composition or method for inducing and maintaining ketonemia or ketosis by ingesting at least 10 grams of the combination of D-BHB, D-BHV, and D-1,3BD of the present disclosure at each meal. In some aspects, the present disclosure includes a composition or method for inducing and maintaining ketonemia or ketosis by ingesting at least 10 grams of the combination of D-BHB, D-BHV, and D-1,3BD of the present disclosure before, during, or after a fasted state of at least 6, 8, 10, or 12 hours.

The present disclose includes a total daily dosage of 50, 60, 70, 80, 90, 100, 110, 120, 130, 140, 150, 160, 170, 180, 190, or 200 grams of the combination of D-BHB, D-BHV, and D-1,3BD of the present disclosure.

In some aspects, the combination of D-BHB, D-BHV, and D-1,3BD of the present disclosure is administered at a dosage of 0.10 to 1 g/kg, 0.12 to 0.8 g/kg, 0.13 to 0.7 g/kg, 0.14 to 0.6 g/kg, 0.15 to 0.5 g/kg per unit dosage. In some aspects, the combination of D-BHB, D-BHV, and D-1,3BD of the present disclosure is administered at a dosage of 0.30 to 3 g/kg, 0.4 to 2.5 g/kg, 0.5 to 2 g/kg, 0.75 to 1.5 g/kg, 0.8 to 1 g/kg per day.

In some aspects, the present disclosure includes compositions for reducing or avoiding side effects such as acidosis and gastrointestinal distress upon ingestion of D-BHB, D-BHV, and D-1,3BD.

In some aspects, the present disclosure includes compositions for reducing or avoiding side effects such as intoxication from 1,3-butanediol by use of the combination of D-BHB, D-BHV, and D-1,3BD of the present disclosure.

According to other methods, a composition including approximately 15% to approximately 85% D-BHB, between substantially no D-BHV to approximately 26% D-BHV, and between approximately 15% to approximately 75% D-1,3BD, such as any of the compositions set forth in the examples (or variants thereof) is administered to a human subject to increase levels of circulating ketones in the blood of the subject. In such compositions, the proportion of D-BHB to D-BHV can be between 1.0 to 0 and 0.7 to 0.3, 0.99 to 0.01, 0.98 to 0.02, 0.97 to 0.03, 0.96 to 0.04, 0.95 to 0.05, 0.9 to 0.1, 0.85 to 0.15, 0.8 to 0.2, or 0.75 to 0.25. Such compositions may be administered using specific carriers, e.g., as described below and illustrated in several examples.

According to another example, the individual constituent components of approximately 15% to approximately 85% D-BHB, between substantially no D-BHV to approximately 26% D-BHV, and between approximately 15% to approximately 75% D-1,3BD may be taken in rapid succession, such that, for example, D-BHB is taken first, D-BHV is taken second, and D-1,3,BD is taken third. According to one example, the D-BHB and D-BHV may be taken first, and the D-1,3BD may be taken second. The D-BHV and D-BHB may be taken simultaneously as a single mixture of these compounds in appropriate amounts. In another example, the D-1,3BD may be taken first, and the D-BHB and D-BHV may be taken second. In other examples, one portion of the composition may be taken 2, 3, or 5 minutes before the other portion of the composition.

In one aspect, the present disclosure involves the described compounds, i.e., (D)-β-hydroxybutyric acid, (D)-β-hydroxyvaleric acid, and/or (D)-1,3 butanediol, that are not in the form of a salt (e.g., not a sodium, magnesium, calcium and/or potassium salt). In one aspect, the present disclosure involves the described compounds, i.e., (D)-β-hydroxybutyric acid, (D)-β-hydroxyvaleric acid, and/or (D)-1,3 butanediol, that are not in the form of an ester. In one aspect, the present disclosure involves compositions comprising (D)-β-hydroxybutyric acid, (D)-β-hydroxyvaleric acid, and/or (D)-1,3 butanediol in a buffer-free composition. In one aspect, the present disclosure involves compositions comprising (D)-β-hydroxybutyric acid, (D)-β-hydroxyvaleric acid, and/or (D)-1,3 butanediol in a lactose-free composition. In one aspect, the present disclosure involves compositions comprising (D)-β-hydroxybutyric acid, (D)-β-hydroxyvaleric acid, and/or (D)-1,3 butanediol in a gluten-free composition. In one aspect, the present disclosure involves compositions comprising (D)-β-hydroxybutyric acid, (D)-β-hydroxyvaleric acid, and/or (D)-1,3 butanediol in a soy-free composition. In one aspect, the present disclosure involves compositions comprising (D)-β-hydroxybutyric acid, (D)-β-hydroxyvaleric acid, and/or (D)-1,3 butanediol in a caffeine-free composition. In one aspect, the present disclosure involves compositions comprising (D)-β-hydroxybutyric acid, (D)-β-hydroxyvaleric acid, and/or (D)-1,3 butanediol in a carbohydrate-free composition. In one aspect, the present disclosure involves compositions comprising (D)-β-hydroxybutyric acid, (D)-β-hydroxyvaleric acid, and/or (D)-1,3 butanediol in a composition free of 3-hydroxybutyl-β-hydroxybutyrate. In one aspect, the present disclosure involves compositions comprising (D)-β-hydroxybutyric acid, (D)-β-hydroxyvaleric acid, and/or (D)-1,3 butanediol in a composition free of 3-hydroxybutyl-3-hydroxy-ethyl butyrate. In one aspect, the present disclosure involves compositions comprising (D)-β-hydroxybutyric acid, (D)-β-hydroxyvaleric acid, and/or (D)-1,3 butanediol in a composition free of 3-hydroxybutyl-3-hydroxy-butanoate. In one aspect, the present disclosure involves compositions comprising (D)-β-hydroxybutyric acid, (D)-β-hydroxyvaleric acid, and/or (D)-1,3 butanediol in a composition free of ketone ester. In one aspect, the present disclosure involves compositions comprising (D)-β-hydroxybutyric acid, (D)-β-hydroxyvaleric acid, and/or (D)-1,3 butanediol in a composition free of acetoacetate.

In one aspect, the present disclosure involves compositions comprising (D)-β-hydroxybutyric acid, (D)-β-hydroxyvaleric acid, and/or (D)-1,3 butanediol in a composition free of the following compound D beta hydroxybutyrate, DL 1,3-butanediol ester.

In one aspect, the present disclosure involves compositions comprising (D)-β-hydroxybutyric acid, (D)-β-hydroxyvaleric acid, and/or (D)-1,3 butanediol in a sugar-free composition. In one aspect, the present disclosure involves compositions comprising (D)-β-hydroxybutyric acid, (D)-β-hydroxyvaleric acid, and/or (D)-1,3 butanediol in a composition free of polyesters of (D)-β-hydroxybutyric acid, (D)-β-hydroxyvaleric acid, and/or (D)-1,3 butanediol. In one aspect, the present disclosure involves compositions comprising (D)-β-hydroxybutyric acid, (D)-β-hydroxyvaleric acid, and/or (D)-1,3 butanediol in a composition free of D ethyl 3-hydroxybutyrate. In one aspect, the present disclosure involves compositions comprising (D)-β-hydroxybutyric acid, (D)-β-hydroxyvaleric acid, and/or (D)-1,3 butanediol in a composition free of medium chain triglycerides. In one aspect, the present disclosure involves compositions comprising (D)-β-hydroxybutyric acid, (D)-β-hydroxyvaleric acid, and/or (D)-1,3 butanediol in a composition free of medium chain fatty acids. In one aspect, the present disclosure involves compositions comprising (D)-β-hydroxybutyric acid, (D)-β-hydroxyvaleric acid, and/or (D)-1,3 butanediol in a composition free of esters of medium chain fatty acids.

In one aspect, the present disclosure involves compositions comprising (D)-β-hydroxybutyric acid, (D)-β-hydroxyvaleric acid, and/or (D)-1,3 butanediol in combination with a sugar alcohol. In one aspect, the present disclosure involves compositions comprising (D)-β-hydroxybutyric acid, (D)-β-hydroxyvaleric acid, and/or (D)-1,3 butanediol in combination with erythritol, sorbitol, mannitol, xylitol, aspartame, stevia glycosides, allulose, monk fruit (also referred to as monk fruit extract), and similar sweeteners having zero or low calories. A sweetener can be "low-calorie", i.e., it imparts desired sweetness when added to a sweetenable composition (such as, for example, as beverage) and has less than 40 calories per 8 oz serving. A sweetener can be "zero-calorie", i.e., it imparts desired sweetness when added to a sweetenable composition (such as, for example, a beverage) and has less than 5 calories per 8 oz. serving, preferably 0 calories per 8 oz. serving.

Compositions based on the above examples may be mixed with a carrier comprising a food or beverage product as illustrated by the examples below. The present disclosure includes products including, but not limited to protein bars, nutritional and sports beverages, fruit juice, zero calorie iced caffeinated beverages, snacks, tea beverages, carbonated beverages, energy gels, and alcoholic beverages. The present disclosure also includes fermented foods and beverages containing the compositions described herein. The preferred compositions may be combined in foods or beverages that exhibit various nutritional criteria such as low-calorie foods and beverages for weight control, low calorie and low carbohydrate for facilitating weight control and/or weight loss, low carbohydrate and/or high fat for those following a ketogenic diet, and high carbohydrate and/or high protein for athletes.

Figure 3:
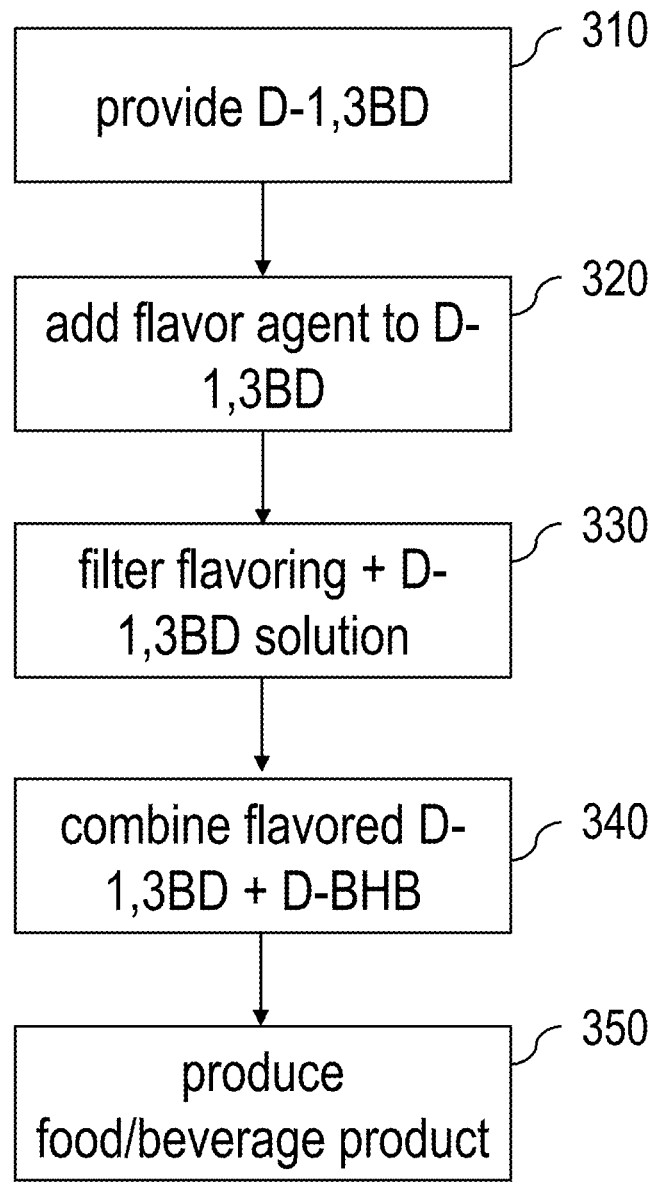
FIG. 3 represents a flow-chart of a process of improving the flavoring of a food or beverage including a ketone body according to one example.

A method of improving the flavor profile of a food or beverage product including ketone bodies includes combining D-1,3BD with D-BHB and optionally D-BHV to achieve a composition that can improve the taste of food or beverage products designed to induce ketosis. An exemplary method is described with reference to the flowchart of FIG. 3. The method can include providing a predetermined amount of D-1,3BD (310). Next, a flavoring agent may be added to the D-1,3BD (320) to create a solution including the D-1,3BD and the desired flavoring. According to one example, the flavoring agent may be a natural flavoring agent such as fruit. The fruit may be fresh fruit or may be freeze dried fruit according to certain examples. The flavoring agent may be added to the D-1,3BD for a predetermined time, where the predetermined time is a time sufficient to obtain a desired flavor profile from the flavor agent. By adding the flavor agent to the D-1,3BD, the D-1,3BD may act as a solvent and allow the flavorings, such as natural flavorings, to enter a resulting solution including the D-1,3BD. After a desired amount of time has elapsed, the resulting solution may be filtered to remove unwanted parts of the flavoring agent such as pulp and fiber (330). This filtration step (330) is optional and the degree of filtering may be adjusted such that some fiber or pulp may remain in the resulting filtered solution.

After the filtered flavored D-1,3BD is produced (step 330), that solution is combined with D-BHB and optionally D-BHV to form a flavored solution of D-1,3,BD, D-BHB, and optionally D-BHV (step 340). The combination of the flavored D-1,3BD and D-BHB and optional D-BHV substantially improves the resulting flavors of D-1,3BD and D-BHB on their own, thus providing ketone bodies for use as additives to food and beverage products (step 350). Those skilled in the art will appreciate that certain of the steps may be combined. For example, step 340 may be combined with step 350. For example, water may be added to D-BHB before the filtered flavored D-1,3BD is added to it, thus forming a flavored water beverage when the flavored D-1, 3BD is added to a solution including a substantial portion of water and D-BHB (with or without D-BHV). In another illustrative example, the D-1,3BD may be in a beverage product, while the D-BHB and D-BHV may be in a food or a semi-liquid product that is to be consumed with the beverage or a predetermined period of time before or after the beverage. Permutations of these combinations are possible and envisioned. Various combinations of these examples may be made so long as the D-BHB, optional D-BHV, and D-1,3BD are administered closely enough in time to give rise to the benefits of the ketotic efficiency observed and expected from the examples described above.

Where a medicament or nutritional product of the invention is for use in a beverage, food, snack bar, gel or the like, it is convenient to use it in the form of a liquid or solid, preferably with a composition having approximately 15% to approximately 85% D-BHB, between substantially no D-BHV to approximately 26% D-BHV, and between approximately 15% to approximately 75% D-1,3BD, including any of the examples, disclosures or combinations thereof. The resulting compositions may be administered in a dosage of greater than about 0.02 g/kg and more preferably between about 0.1 to about 0.9 g/kg.

The present invention will now be described further by way of illustration only by reference to the following examples. Further embodiments falling within the scope of the invention will occur to those skilled in the art in light of these. Each of these examples is expected to increase blood ketone levels by about 1.5 mMol, sustained for approximately 30 minutes and tapering over the course of 3 hours. For example, a person may achieve and maintain a ketone body level of about 1.3, 1.4, 1.5, 1.6, 1.7, 1.8, 1.9, 2.0, 2.1, 2.2, 2.3, 2.4, 2.5 mM or higher according to the methods of the present disclosure.

Example 1: Snack Bar

A 50% solution (D)-β-hydroxybutyric acid (36 g)+(D)-β-hydroxyvaleric acid (4 g) (one having 48% D-BHB+2% D-BHV and 50% water) was stirred into (D)-1,3 butanediol (20 g), peanut butter (118 g), maple syrup (30 g), and vanilla extract (5 g) in a large mixing bowl. Dry ingredients were then added, including 1¼ cups rolled oats, 2 tbsp chia and flax seed blend, ¼ tsp salt, and ½ cup chocolate chips. The mixture was then cooled for 30 minutes, the dough portioned into 1 inch×3 inch bars on a baking sheet and baked at 175° F. for 60 minutes.

Example 2: Preparation of a Nutritional Beverage

The flavoring was prepared by adding freeze dried passion fruit (33 g) freeze dried pineapple (27 g) to (D)-1,3 butanediol (300G) and allowing to rest for 48 hours such that the fruit flavors are absorbed into the solution. The solution is then filtered to remove the fiber and pulp. The flavoring was stirred into a solution of (D)-β-hydroxybutyric acid (288 g), (D)-β-hydroxyvaleric acid (12 g), and water (2173 g) using a 5 gallon blending container and magnetic stirrer. Buffers and sweeteners were then blended into the solution in the amounts of 20 g sodium bicarbonate, 30 g potassium bicarbonate, and 420 g erythritol to concentrate. Carbonated water was then added in the amount of 3310 g. The equipment used to make these products is not critical to the invention and is being provided by way of example only. For example, an immersion blender may be used instead of a magnetic stirrer and may achieve better results, particularly when making larger batches of material and to achieve better blending.

Example 3: Sports Energy and Hydration Beverage

A beverage was prepared by combining (D)-β-hydroxybutyric acid (40 g) with (D)-1,3 butanediol (44 g) and water (2,180 g). Sodium, potassium and calcium salts of (D)-β-hydroxybutyric acid were then added to the solution in the amounts of 4 g, 6 g and 6 g respectively. For the ketogenic ingredients, this equates to molar proportions of 50% (D)-β-hydroxybutyric acid (10% in salt form), and 50% (D)-1,3 butanediol. Flavorings and sweetener in the form of 6.6 g pineapple, 7.5 g passionfruit and 110 g of erythritol were then added to the solution.

Example 4: Energy Gel

The following ingredients were mixed: 50% solution (D)-β-hydroxybutyric acid (60 g)+(D)-β-hydroxyvaleric acid (20 g) was stirred into (D)-1,3 butanediol (40 g), brown rice syrup (½c), barley malt (½c), unrefined coconut oil (¼c), creamy peanut butter (¼c), and salt (1 tsp). The mixture was heated to between 130 and 150° F. over medium-low heat for 3-5 minutes until the ingredients were well combined and achieved a low viscosity. Warm water between (130 and 150° F.) (¼c) was added to the jar and mixed vigorously until well combined and no separation was observed.

Example 5: Alcoholic Beverage

A 45% solution (D)-β-hydroxybutyric acid (80 g) with (D)-β-hydroxyvaleric acid (20 g) (one having 44% D-BHB+11% D-BHV and 45% water) was stirred into (D)-1,3 butanediol (100 g). Water and flavoring were then added to create a concentrate in the amounts of 243 g water, 45 g monk fruit, and 6 g lime concentrate. Silver tequila was then added in the amount of 450 ml.

Example 6: Iced Coffee Beverage

50% solution (D)-β-hydroxybutyric acid (14.4 g)+(D)-β-hydroxyvaleric acid (0.6 g) (one having 48% D-BHB, 2% D-BHV and 50% water) was blended into (D)-1,3 butanediol (15 g) and MCT oil (15 g) using an emersion blender. The mixture was then added to 4 oz chilled espresso and 4 oz cold water.

Example 7: Extended Release Foods

Smoothies have been made to extend release of the ketones as follows:
Green Tart Ketone Smoothie
1 cup water
¼ cup coconut milk
4 romaine lettuce leaves
1 medium green apple
1 stalk celery
½ cup cucumber
1 handful watercress (or use spinach)
10 g D-1,3 butanediol
10 g D-b-hydroxybutyric acid and (D)-β-hydroxyvaleric acid
juice of 1 lime
Cherry Limeaid Ketone Smoothie
1 ripe nectarine or peach
1 heaping cup fresh or frozen cherries
¾ cup almond milk
1 medium lime
10 g D-1,3 butanediol
10 g D-b-hydroxybutyric acid and (D)-β-hydroxyvaleric acid
1 handful ice
Blueberry Breakfast Tart Smoothie
2¼ cups unsweetened almond milk
⅓ cup raw unsalted cashews, soaked
⅓ cup rolled oats
2 tablespoons pure maple syrup
½ teaspoon ground cinnamon
2 cups frozen blueberries
10 g D-1,3 butanediol
10 g D-b-hydroxybutyric acid and (D)-β-hydroxyvaleric acid
Gummies
227 g granulated sugar
27 g sorbitol
227 g corn syrup glucose,
135 g D-BHB solution (one having 48% D-BHB, 2% D-BHV and 50% water)
90 g D-1,3BD
44 grams gelatin
1.5 teaspoon candy flavoring
In one aspect, gummies can be made by the following steps:
Combine gelatin, D-1,3BD and the D-BHB solution in a heatproof container. Stir gently to combine. Let sit for 5 minutes to give your gelatin time to bloom.
Combine together the corn syrup, sugar, and sorbitol in a medium saucepan. Stir gently to combine. Bring to a simmer on medium heat.
Remove the mixture from the heat and stir in the D-BHB/gelatin mixture with a spatula until gelatin is melted.
Let the mixture sit for 10 minutes and allow the mixture to clear and foam to collect at the top. After 10 minutes the foam should be able to be easily scooped off the surface with a spoon.
Add any coloring or candy flavorings.
Pour mixture into candy molds.
Chill in the fridge for 24 hours.

Example 8: Avoiding Sleep Loss Side Effects

The following compositions are made into a consumable beverage and ingested by a panel of human test subjects two times per day at breakfast and after lunch each day for one week:

| Composition # | Concentration of DBHB + DBHV in a compositing containing DBHB + DBHV and D-1,3BD |
|---|---|
| 1 | 100% |
| 2 | 45% |
| 3 | 0% |

The panelists record their number of hours of sleep and sleep quality during each night of the test week. The panelists are then assigned to a different group during week two and record their number of hours of sleep and sleep quality during each night of the second test week. The panelists are then assigned to a different group during week three and record their number of hours of sleep and sleep quality during each night of the third test week. The results are then compared both between the same panelists during each week as well as an average of all panelists for each composition. The comparisons show that ingestion of composition 2 produces higher quality sleep (higher percentage SWS, REM) and longer sleep than compositions 1 and 2.

Example 9: Avoiding Gastrointestinal Side Effects

The following compositions are made into a consumable beverage and ingested by a panel of human test subjects two times per day at breakfast and after lunch each day for three days:

| Composition # | Concentration of DBHB + DBHV in a compositing containing DBHB + DBHV and D-1,3BD |
|---|---|
| 1 | 100% |
| 2 | 45% |
| 3 | 0% |

The panelists record gastrointestinal discomfort during each night of the test period. After a one-day washout period, the panelists are then assigned to a different group during the second three day test period and record their gastrointestinal discomfort during each night of the second test period. After a one-day washout period, the panelists are then assigned to a different group during the third three-day test period and record their gastrointestinal discomfort during each night of the third test period. The results are then compared both between the same panelists during each test period as well as an average of all panelists for each composition. The comparisons show that ingestion of composition 2 produces less gastrointestinal discomfort than compositions 1 and 2.

Example 10: Improvements in Tolerability

The following compositions are made into a consumable beverage and ingested by a panel of human test subjects:

| Composition # | Concentration of DBHB + DBHV in a compositing containing DBHB + DBHV and D-1,3BD |
|---|---|
| 1 | 100% |
| 2 | 45% |
| 3 | 0% |

Panelists are asked to consume as much of the consumable beverages as tolerable up to a maximum dosage of 150 grams of the compositions per day for as many consecutive days as they can tolerate. The panelists record the amounts of the consumable beverages consumed each day and the number of consecutive days the consumable beverages are consumed. After a one-week washout period, the panelists are then switched to a different composition # and asked to repeat the procedure for a second period. After a one-week washout period, the panelists are then switched to a different composition # and asked to repeat the procedure for a third period. The comparisons show that panelists tolerate ingestion of composition 2 for significantly longer than compositions 1 and 2 and are able to tolerate ingestion of at least 100 g per day of composition 2 whereas panelists are unable to tolerate ingestion of 100 g per day of compositions 1 and 3.

Example 11: Taste and Tolerability Comparison

The following compositions were made and tested by a panel of 10 blinded taste testers for tolerability and taste according to the following scales 1. The quality of the flavor of the product on a scale of 1 to 5? (1-terrible, 2-bad, 3-tolerable, 4-good, 5-excellent)
2. Ability to finish the entire 8 oz beverage (1-could not finish, 2-finished with difficulty, 3-finished reluctantly, 4-easily finished 5-very easily finished
3. Rank all the compositions by preference (1-worst, 2-fourth best, 3-third best, 4-second best, 5-best)

All compositions were prepared as 8 ounce beverages. They all contained an equivalent amount (10 grams) of total active ingredients comprised of differing blends of ketogenic agents. In addition, each composition contained the exact same amounts and types of inactive ingredients, including carbonated water, sweetener and natural flavoring. The natural flavoring contained a blend of tropical and citrus fruit juices. The ratios of active ingredients were varied for each composition as shown in the following tables:

Beverage 1 of the present disclosure containing:
48% BHB acid, 2% BHV acid, 50% 1,3BD

| | molar mass | molar % ratio | g/mol | weight ratio | g/serving |
|---|---|---|---|---|---|
| BHB Acid | 104.1045 | 48.0% | 49.97 | 51.3% | 5.1 |
| BHV Acid | 118.06 | 2.0% | 2.36 | 2.4% | 0.2 |
| 1,3 BD | 90.12 | 50.0% | 45.06 | 46.3% | 4.6 |
| | | 100.0% | 97.39 | 100.0% | 10.0 |

Beverage 2 of the present disclosure containing:
72% BHB acid, 3% BHV acid, 25% 1,3BD

| | molar mass | molar % ratio | g/mol | weight ratio | g/serving |
|---|---|---|---|---|---|
| BHB Acid | 104.1045 | 72.0% | 74.96 | 74.2% | 7.4 |
| BHV Acid | 118.06 | 3.0% | 3.54 | 3.5% | 0.4 |
| 1,3 BD | 90.12 | 25.0% | 22.53 | 22.3% | 2.2 |
| | | 100.0% | 101.03 | 100.0% | 10.0 |

Beverage 3 of the present disclosure containing:
24% BHB acid, 1% BHV acid 75% 1,3BD

| | molar mass | molar % ratio | g/mol | weight ratio | g/serving |
|---|---|---|---|---|---|
| BHB Acid | 104.1045 | 24.0% | 24.99 | 26.6% | 2.7 |
| BHV Acid | 118.06 | 1.0% | 1.18 | 1.3% | 0.1 |
| 1,3 BD | 90.12 | 75.0% | 67.59 | 72.1% | 7.2 |
| | | 100.0% | 93.76 | 100.0% | 10.0 |

Comparative Beverage 1 of US20180057846 containing:
60% BHB acid, 30% BHB salts (32% sodium, 44% potassium, 24% calcium), 10% 1,3 BD

| | molar mass | molar % ratio | g/mol | weight ratio | g/serving |
|---|---|---|---|---|---|
| BHB Acid | 104.1045 | 60% | 62.46 | 52% | 5.2 |
| BHB sodium | 127.09 | | 12.20 | 10% | 1.0 |
| BHB potassium | 142.19 | 30% | 18.77 | 16% | 1.6 |
| BHB calcium | 246.27 | | 17.73 | 15% | 1.5 |
| 1,3 BD | 90.12 | 10% | 9.01 | 7% | 0.7 |
| | | 100% | 120.18 | 100% | 10.0 |

Comparative Beverage 2 of US20180057846 containing: 90% BHB acid, 10% 1,3BD

| | molar mass | % ratio | g/mol | weight ratio | g/serving |
|---|---|---|---|---|---|
| BHB Acid | 104.1045 | 90.0% | 93.69 | 91.2% | 9.1 |
| 1,3 BD | 90.12 | 10.0% | 9.01 | 8.8% | 0.9 |
| | | 100.0% | 102.71 | 100.0% | 10.0 |

Presentation: All compositions were presented simultaneously and at the same refrigerated temperature. They were presented in the same type of cup which were labeled with A, B, C, D and E:

A=Beverage 1 of present disclosure
B=Beverage 2 of present disclosure
C=Beverage 3 of present disclosure
D=Beverage 1 of US20180057846
E=Beverage 2 of US20180057846

Method: Participants were seated separately from each other and instructed to not communicate amongst themselves. Their stations had a cup of drinking water, a questionnaire and a pen/pencil.

The taste test coordinator presented each participant with all 5 compositions (in the manner described above) and monitored the participants to ensure the procedure was followed properly.

The participants cleansed their palate with water, tasted product A and recorded their answers in the 'Product A Questionnaire'. They repeated this process with products B-E. Then, participants answered the final overall questions in the 'Overall Experience Questionnaire'. Questionnaire responses were anonymous.

| | Table of comparative taste and tolerability results. Values are average of 10 participants | | | | | | |
|---|---|---|---|---|---|---|---|
| | Quality of flavor | | Ability to finish beverage | | Preference ranking | | Total average |
| Sample | Average | Std Dev | Average | Std Dev | Average | Std Dev | score |
| Beverage 1 of present disclosure | 4.8 | 0.40 | 5.0 | 0.00 | 4.9 | 0.30 | 15.1 |
| Beverage 2 of present disclosure | 3.7 | 0.46 | 3.6 | 0.49 | 3.0 | 0.63 | 11.2 |
| Beverage 3 of present disclosure | 4.2 | 0.40 | 4.1 | 0.54 | 4.0 | 0.45 | 13.2 |
| Beverage 1 of US20180057846 | 1.9 | 0.70 | 2.3 | 0.90 | 1.3 | 0.46 | 7.1 |
| Beverage 2 of US20180057846 | 2.1 | 0.54 | 2.6 | 0.92 | 1.7 | 0.46 | 7.9 |

Example 12: Taste and Tolerability Comparison

The following compositions are made and tested by a panel of 10 blinded taste testers for tolerability and taste according to the following scales
1. the quality of the flavor of the product on a scale of 1 to 5? (1-terrible, 2-bad, 3-tolerable, 4-good, 5-excellent)
2. Ability to finish the entire 8 oz beverage (1-could not finish, 2-finished with difficulty, 3-finished reluctantly, 4-easily finished 5-very easily finished
3. Rank all the compositions by preference (1-worst, 2-fourth best, 3-third best, 4-second best, 5-best)

All compositions are prepared as 8 ounce beverages. They all contain an equivalent amount (10 grams) of total active ingredients comprised of a differing blends of ketogenic agents. In addition, each composition contains the exact same amounts and types of inactive ingredients, including carbonated water, sweetener and natural flavoring. The natural flavoring contains a blend of tropical and citrus fruits. The ratios of active ingredients are varied for each composition as shown in the following tables:

| | Beverage 4 of the present disclosure containing: 50% BHB acid, 50% 1,3BD | | | | |
|---|---|---|---|---|---|
| | molar mass | molar % ratio | g/mol | weight ratio | g/serving |
| BHB Acid | 104.1045 | 50.0% | 52.05 | 53.6% | 5.4 |
| 1,3 BD | 90.12 | 50.0% | 45.06 | 46.4% | 4.6 |
| | | 100.0% | 97.11 | 100.0% | 10.0 |

| | Comparative Beverage 2 of US20180057846 containing: 90% BHB acid, 10% 1,3BD | | | | |
|---|---|---|---|---|---|
| | molar mass | % ratio | g/mol | weight ratio | g/serving |
| BHB Acid | 104.1045 | 90.0% | 93.69 | 91.2% | 9.1 |
| 1,3 BD | 90.12 | 10.0% | 9.01 | 8.8% | 0.9 |
| | | 100.0% | 102.71 | 100.0% | 10.0 |

Presentation: All compositions were presented simultaneously and at the same refrigerated temperature. They were presented in the same type of cup and were labeled with A and B.

A=Beverage 4 of present disclosure

B=Comparative Beverage 2 of US20180057846

Method: Participants were seated separately from each other and instructed to not communicate amongst themselves. Their stations had a cup of drinking water, a questionnaire and a pen/pencil.

The taste test coordinator presented each participant with all 5 compositions (in the manner described above) and monitored the participants to ensure the procedure was followed properly.

The participants cleansed their palate with water, tasted product A and recorded their answers in the 'Product A Questionnaire'. They repeated this process with product B. Then, participants answered the final overall questions in the 'Overall Experience Questionnaire'. Questionnaire responses were anonymous.

| | Table of comparative taste parameters. Values are average of 10 participants | | | | | | |
|---|---|---|---|---|---|---|---|
| | Quality of flavor | | Ability to finish beverage | | Preference rankkng | | Total average |
| Sample | Average | Std Dev | Average | Std Dev | Average | Std Dev | score |
| Beverage 4 of present disclosure | 4.8 | 0.6 | 5.0 | 0.0 | 5.0 | 0.0 | 15.4 |
| Beverage 2 of US20180057846 | 2.5 | 0.5 | 2.0 | 0.6 | 1.0 | 0.0 | 6.6 |

Those skilled in the field will understand based on the present disclosure that the various examples above may be scaled and altered to achieve desired results to serve specific purposes. For example, the recipes above may be scaled up for commercial purposes and adjustments may be made to accommodate production on large scale equipment such as adjustments to time, temperature, and amounts of materials without departing from the scope and spirit of the present disclosure.

While the subject matter of this disclosure has been described and shown in considerable detail with reference to certain illustrative embodiments, including various combinations and sub-combinations of features, those skilled in the art will readily appreciate other embodiments and variations and modifications thereof as encompassed within the scope of the present disclosure. Moreover, the descriptions of such embodiments, combinations, and sub-combinations is not intended to convey that the claimed subject matter requires features or combinations of features other than those expressly recited in the claims. Accordingly, the scope of this disclosure is intended to include all modifications and variations encompassed within the spirit and scope of the following appended claims.

The invention claimed is:

1. A beverage or food product comprising, per serving, 3 to 7 grams of (D)-β-hydroxybutyric acid and 0.5 to 8 grams of (D)-1,3 butanediol and 100 to 250 grams of a consumable carrier.

2. The beverage or food product of claim 1, wherein the consumable carrier comprises water or carbonated water, a flavoring agent, and a sweetener.

3. The beverage or food product of claim 2, wherein the sweetener is a sugar alcohol, stevia, allulose, monk fruit, or a combination thereof.

4. The beverage or food product of claim 1, wherein the beverage or food product is free of salts of (D)-β-hydroxybutyric acid.

5. The beverage or food product of claim 1, wherein the beverage or food product is free of esters of (D)-β-hydroxybutyric acid, (D)-β-hydroxyvaleric acid, and (D)-1,3 butanediol.

6. The beverage or food product of claim 1, further comprising (D)-β-hydroxyvaleric acid.

7. The beverage or food product of claim 1, comprising (D)-β-hydroxybutyric acid, (D)-β-hydroxyvaleric acid, and (D)-1,3 butanediol in a molar ratio range of 3 to 7:0.01 to 1:7 to 3 or 4 to 6:0.1 to 0.8:6 to 5.

8. The beverage or food product of claim 7, wherein at least 5% of the (D)-β-hydroxyvaleric acid is in the form of a magnesium salt, potassium salt, calcium salt, or combination thereof.

9. The beverage or food product of claim 1, wherein the beverage or food is in the form of a protein bar, a sports beverage, gummies, or an energy gel.

10. The beverage or food product of claim 1, wherein the beverage or food comprises:
   a) 25% to 85% by weight of (D)-β-hydroxybutyric acid;
   b) 15% to 75% by weight (D)-1,3 butanediol, wherein the flavor of the composition is improved over an equivalent weight of either (D)-β-hydroxybutyrate or (D)-1,3 butanediol alone and over salts and esters thereof.

11. The beverage or food product of claim 10, wherein a) is 55% to 45% and b) is 45 to 55% of the composition by weight.

12. The beverage or food product of claim 10, wherein a) is 65% to 35% and b) is 35 to 65% of the composition by weight.

13. The beverage or food product of claim 10, wherein a) is 70% to 30% and b) is 30 to 70% of the composition by weight.

14. The beverage or food product of claim 10, wherein a) and b) are in a molar ratio of 7:3 to 3:7 or 4:6 to 6:4.

15. A method of making the beverage or food product of claim 1, comprising mixing 3 to 7 grams of (D)-β-hydroxybutyric acid with 0.5 to 8 grams of (D)-1,3 butanediol and 100 to 250 grams of a consumable carrier.

16. The method of claim 15, wherein the beverage or food product comprises a mixture of the (D)-β-hydroxybutyric acid and (D)-1,3 butanediol in a molar ratio of 1:8 to 11 to water or carbonated water.

17. The method of claim 15, wherein the beverage or food product comprises a mixture of the (D)-β-hydroxybutyric acid and (D)-1,3 butanediol in a molar ratio of 1:0.05 to 0.12 to a flavoring agent.

18. The method of claim 15, wherein the beverage or food product comprises a mixture of the (D)-β-hydroxybutyric acid and (D)-1,3 butanediol in a molar ratio of 1:0.6 to 1.2 to a sweetener selected from a sugar alcohol, stevia, allulose, monk fruit, or a combination thereof.

19. A method for increasing ketotic efficiency in a human body comprising:
   administering the beverage or food of claim 1, wherein the ketotic efficiency according to formula I $\Sigma_{t=0}^{n}$ (mMol/L)/(g/kg)*t [Formula I] in the human subject is at least 40% higher than the administration of an equivalent weight of either (D)-β-hydroxybutyrate or (D)-1,3 butanediol alone at one hour after administration.

20. A method of elevating circulating ketone levels by at least 1.4 mM in a human subject within 2 hours of administration comprising administering the food or beverage of claim 1 to the human subject in a serving that comprises at least 10 grams of (D)-β-hydroxybutyric acid and (D)-1,3 butanediol in a molar ratio of 7:3 to 3:7.

* * * * *